United States Patent [19]

Gaffar

[11] 4,431,628
[45] Feb. 14, 1984

[54] NATURAL DYE INDICATOR FOR DENTAL PLAQUE

[75] Inventor: Maria C. S. Gaffar, Somerset, N.J.

[73] Assignee: Colgate-Palmolive Company, New York, N.Y.

[21] Appl. No.: 139,935

[22] Filed: Apr. 11, 1980

Related U.S. Application Data

[63] Continuation of Ser. No. 894,294, Apr. 7, 1978, abandoned.

[51] Int. Cl.³ ............... G01N 31/00; G01N 31/22; G01N 33/48; A61K 7/16
[52] U.S. Cl. ..................................... 424/7.1; 424/49
[58] Field of Search .................... 424/7, 49, 7.1

[56] References Cited

U.S. PATENT DOCUMENTS

| | | | |
|---|---|---|---|
| 3,309,274 | 3/1967 | Brilliant | 424/7 |
| 3,624,219 | 11/1971 | Perlitsh | 424/7 |
| 3,723,613 | 3/1973 | Block | 424/7 |
| 4,132,793 | 1/1979 | Haber | 426/250 |

OTHER PUBLICATIONS

Bouquet, Rev. Francaise d'odo-stomatologie, vol. 18, Dec. 1971, pp. 1239-1261.
Auslander et al., Drug & Cos Ind. Part I, Nov. 1977, pp. 36, 38, 40, 105, 114; Part II, Dec. 1977, pp. 55, 56, 58, 60, 138, 140.
Kieser et al., J. of Clin. Periodont., vol. 3, 1976, pp. 200-207.
Arnim, J. Peridont., vol. 34, 1963, pp. 227-245.
Cohen, J. Peridont., vol. 43, 1972, pp. 333-338.
Chem. Abs. 8th Coll. Index, pp. 1922S-1923S (1967-1971).
Chem. Abs., 9th Coll. Index, pp. 658GS-659GS (1972-1976).
Conn. Biol. Stains, Biotech. Pub. Geneva N.Y., 1946, p. 66.
Mayer, The Chem. of Natural Coloring Matters, Reinhold Pub., N.Y., 1943, pp. 232, 233.

*Primary Examiner*—Albert T. Meyers
*Assistant Examiner*—Kathleen S. McCowin
*Attorney, Agent, or Firm*—Robert L. Stone; Murray M. Grill; Herbert S. Sylvester

[57] ABSTRACT

Plaque disclosing compositions containing the natural red dye from sugar beets as the disclosant, and the process of treating the oral cavity therewith.

5 Claims, No Drawings

NATURAL DYE INDICATOR FOR DENTAL PLAQUE

This is a continuation of application Ser. No. 894,294 filed Apr. 7, 1978, now abandoned.

This invention relates to plaque disclosing compositions in the form of tablets, solutions, gels or aerosols containing the natural dye from sugar beets for use as a diagnostic tool and in the improvement of oral hygiene practices.

PRIOR ART

Dental plaque which forms on tooth surfaces and restorations are colonies of harmful bacteria, which cannot be flushed away by simply rinsing with water. Active brushing of the teeth is required to remove said adherent plaque.

It is a well accepted fact that dental plaque when allowed to accumulate on tooth surfaces can eventually lead to gingivitis, periodontal disease, caries and calculus. Thus, it is apparant that effective removal of deposits of dental plaque is absolutely essential for oral health. Accordingly, proper oral hygiene practices which may be carried out by an individual on his or her own teeth or by a dentist, necessitates readily available means of identification and location of plaque deposits in the oral cavity.

Since dental plaque is usually transparant and colorless and not easily visible, an individual frequently is not aware of the quantity or the location of dental plaque present in the mouth. Therefore, it is desirable to use plaque-disclosing compositions to identify areas of the mouth where plaque buildup is a problem. The use of disclosing compositions motivate a person in the early removal of dental plaque by showing the presence and quantity of plaque.

Accordingly, dye indicators for dental plaque as a means of measuring tooth cleanliness and to effect proper oral hygiene practices, have been widely explored in the prior art.

Disclosing agents that are currently available commercially are organic dyes such as erythrosin (FDC Red #3) as disclosed in U.S. Pat. No. 3,309,274 by Brilliant, and U.S. Pat. No. 3,624,219 by Perlitsch. The Perlitsch patent prefers the erythrosin to Amaranth or Brilliant Blue because the latter dyes are excessively water soluble and do not penetrate or persist in the mouth to the degree desirable for plaque-disclosing purposes. The Brilliant patent utilizes the fluorescent synthetic dyes, FDC colors Red #3, Green #8, Red #19, Red #22, Red #28, Yellow #7 and Yellow #8, which are invisible to the naked eye under normal daylight or artificial light, and only becomes visible by using light of the proper wave length. When appropriately filtered light strikes the fluorescent dye, any tartar, calculus, decay, etc. will glow brightly in its respective color. Certain natural colors such as chlorophyll and carotene can also be used, but are not preferred because they do not fluoresce as well and are subject to breakdown.

There are many articles assessing the various known disclosing agents such as a paper by Sumter S. Arnim in the Journal of Periodontology 34, 227–245, 1963, entitled "The Use of Disclosing Agents for Measuring Tooth Cleanliness", wherein a palatable, food color tablet of FDC Red #3 (erythrosin) is recommended as the dye of choice over fuchsin, merbromin and neutral red for use in teaching personal oral hygiene and in the prevention of dental disease. Merbromin was found to be a poor discloser, did not taste good and the dye was hard to remove from the mouth. Neutral red was also objected to because it stained the urine red. Fuchsin is a suspected carcinogen, whereas FDC Red #3 is certified by the Food and Drug Administration.

A subsequent article by D. Walter Cohen et al in the Journal of Periodontology 43, 333–338, 1972 entitled "A Comparison of Bacterial Plaque Disclosants in Periodontal Disease", compares the erythrosin dye (FDC Red #3) with Sodium Fluorescein (FDC Yellow #8), a new disclosant developed by Brilliant. A major objection to the erythrosin dye is the prolonged retention of unsightly color in the patient's mouth. This problem is eliminated with the use of sodium fluorescein, since the plaque stained therewith is color free and becomes visible only upon exposure to a special filtered light whereby the plaque fluoresces a bright yellow.

The Block patents U.S. Pat. Nos. 3,723,613 and 4,064,229 also objected to the erythrosin dyes as a disclosing agent because of the poor contrast between the gingival tissues and the stained plaque and consequently developed a two-tone dye test comprising the combination of the FDC Red #3 (erythrosin) with either FDC Green #3, FDC Blue #1 or Hercules Green Shade 3 in order to obtain differential staining, i.e. thick old plaques stain blue and thin new plaques stain red.

However, a more recent study by J. B. Kieser and A. Bryan Wade reported in the Journal of Clinical Periodontology 3, 200–207, 1976, entitled "Use of food colourants as plaque disclosing Agents", assessed the effectiveness of certain food colorants as plaque disclosing agents in comparison with erythrosin and other known proprietary disclosing agents. It was found that the blue range of food colorants compared favorably with the best of the proprietary disclosing agents, were more readily and cheaply available, and the taste of the food colorants were more acceptable. However, the main ingredient of the blue range of food colorants has been prohibited for use by FDC regulations.

Accordingly, a disclosant dye must meet certain criteria in order to be useful as a plaque disclosing agent. Firstly, the dye must be capable of adequately penetrating the plaque deposit and stain said plaque so as to be readily visible to the user, without producing an excessively prolonged staining effect. This staining efficacy must be selective so as to identify the areas of plaque-formation on all tooth surfaces and not stain gingival or other oral tissues. This selective staining efficacy must be coupled with easy removability from the mouth by simply washing or rinsing after use. In addition, the taste must be pleasant and acceptable to the user, and the color must be pleasing. Lastly, it must be harmless and non-toxic.

It is evident that certain of the prior art plaque-disclosants meet some of the above criteria, but not all. Erythrosin, the most popularly used disclosing dye has the disadvantages of unpleasant taste, non-discriminatory staining of the gingival tissues, and is difficult to remove from gingival tissues and oral surfaces.

It is also known to use a crystalline sugar such as lactose which is less soluble than cane or beet sugar as the water soluble grit (abrasive) in a dentifrice, as disclosed by U.S. Pat. No. 1,211,712 by Keefe. This crystalline sugar replaces the conventional insoluble abrasives such as chalk, pumice, cuttle fish, whiting, etc. and is present in large amounts, i.e. 15 parts in a total of 20 parts or 75% of the total composition. However, there is no disclosure of the red dye from sugar beets as an ingredient in dentifrice formulations generally, nor as a disclosing agent for dental plaque specifically.

DESCRIPTION OF THE INVENTION

It has now been found that the natural dye from sugar beets overcomes the many disadvantages inherent in prior art plaque-disclosants, and possesses the desirable properties of a superior dental plaque dye indicator.

Accordingly, it is an object of this invention to provide an improved plaque-disclosing means which selectively stains plaque-formation on all tooth surfaces, without staining adjacent gingival tissues.

Another object of this invention is to provide an improved plaque-disclosing composition which rinses off easily.

Still another object of this invention is to provide a pleasant tasting plaque-disclosing composition.

Still another object of this invention is to provide a disclosing agent from a natural vegetable source and not a synthetic organic dye.

Another object of this invention is to provide a novel process for safely and easily applying plaque-disclosing compositions so that dental plaque can readily be identified by the user.

Still another object of this invention is to provide the individual with a simple and efficient means of maintaining oral health.

Other objects of this invention will become obvious to those skilled in the art upon reading the following specification.

Accordingly, the present invention relates to dental plaque disclosing compositions containing an effective staining amount of the natural dye from sugar beets in a physiologically acceptable vehicle, which may be in the form of a solution, tablet, gel, powder or aerosol.

The disclosing agent utilized in instant invention is obtained from the natural vegetable source, sugar beets, and is not a synthetic organic dye. The red vegetable colorant obtained from sugar beets renders plaque on teeth visible to the naked eye immediately upon contact therewith, (i.e. brushing or rinsing or chewing), without staining the gingival or other adjacent oral tissues and rinses off easily. This selective staining is coupled with a more pleasant taste than formulations containing prior art synthetic organic dyes.

The red dye obtained from the red beet has been defined by Fritz Mayer, "The Chemistry of Natural Coloring Matters", Translated and Revised by A. H. Cook, "American Chemical Society Monograph Series", 1943, as betanin, a nitrogenous anthocyan, which forms glistening bronze-green crystals. Betanin may be degraded to glucose and betanidin, $C_{20}H_{23}O_7N_2Cl$.

Red beet root contains both red and yellow pigments belonging to the class known as betalaines as described in Drug and Cosmetic Industry, November 1977, pages 105 and 114. Betalaines are quaternary ammonium amino acids. This class is divided into betacyanines (red) and betaxanthines (yellow). Betacyanine concentration far exceeds that of the betaxanthines. Major betacyanine pigment is betamine constituting 75 to 95% of the betacyanine content. Structure of betamine is represented as shown below:

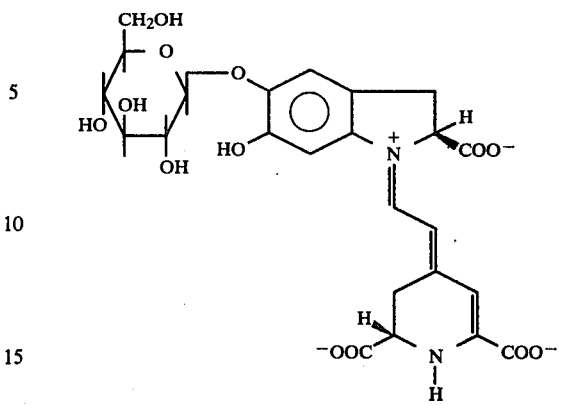

The red beet color is deep red with a somewhat purplish hue. The color intensity varies depending upon physical form (i.e., dehydrated red beet powder, liquid beet juice concentrate and spray dried extracts). Many horticultural practices influence the quantity of pigment in the root tissue, the average content being estimated to be approximately 1 gm/100 gm of total solids or 120 mg/100 gm based on fresh weight. It should be noted that all betalaine pigments are water soluble.

Present commercial products are, in the main, either liquid beet juice concentrates produced by concentrating the juice under vacuum to a total solids content of 40 to 60 percent, or powders produced by spray drying the concentrate. Ascorbic acid usually is added as a stabilizer, sodium propionate as a preservative.

On a dry weight basis, betamine content of these extracts is between 0.4 and 1.0 percent, the remaining solids being mainly sugar (80 percent), ash (8 percent) and crude protein (10 percent). Color strength of betamine based on absorbance: $A_{1\,cm}^{1\%}$ is equal to or greater than currently used artificial red dyes.

A plaque disclosant of a natural vegetable dye made from sugar beets useful in this invention is typically commercially available from the Beatrice Foods Company, Special Products Division, Chicago, Ill., is a liquid concentrate or powder and has FDA approval.

Color-Treme R-111 and R-333 are both color concentrates naturally extracted from beet juice by a special process. This process minimizes the decomposition of the color components. The color analysis of beet juice by measuring the absorbance at the following 3 wavelengths:
1. 476 nm (Yellow-Vulgaxanthin)
2. 538 nm (Bluish Red-Betamine)
3. 600 nm (Background), using a 1 cm optical cell and 0.05 M KH Phthalate Buffer (pH 4.0) or distilled water for sample dilutions, resulted in absorbance readings of 0.30, 0.44 and 0.045 respectively, and a calculated concentration of 38.7 mg/100 ml Betamine and 20.4 mg/100 ml Vulgaxanthin, a ratio of Betamine to Vulgaxanthin of 1.90 to 1.

Color-Treme R-333 is a dark pink to red powder, free of hard lumps, and passes through a number 10 U.S. standard sieve, and consists of 40–50% beet juice concentrate, 1% citric acid and 40–50% dextrin (carrier), with an active color concentration of 0.35%. The active color consists of the ratio of betamine to vulgaxanthin. The citric acid functions as a color stabilizer and processing aid. R-111 is added to dextrin which serves as a carrier.

Color-Treme R-111 is a red colored concentrate containing 65-70% beet juice concentrate, 2% citric acid and 28-33% water with an active color concentration of 0.5%. This aqueous solution may exhibit precipitation upon exposure to light which is a result of microbial growth. It is accordingly advantageous to add preservatives such as sodium benzoate or place in the dark, in order to prevent the solution from decomposing upon exposure to light.

Color-Treme is incompatible with metals such as iron, copper, zinc, aluminum, and with acids such as propionic acid and adipic acid. A concentration of Color-Treme in food products up to 2% will not impart the characteristic odor, taste and smell of sugar beets. The pH of Color-Treme may vary within the range of 3.2 to 6.0, and preferably 5.5 to 6.0. A 1.0% solution of Color-Treme powder in water has a pH of 4.4. A color change is noted when the pH goes to the basic side (greater than pH 7 with the addition of drops of 0.1 N NaOH). The deep red color changes to dark purple.

The liquid concentrate (R-111) as is, and in aqueous dilutions of 1:5 and 1:10 have been tested on plaque grown in vitro on human extracted teeth incubated in a medium containing a plaque-forming microorganism, *Actinomyces viscosus*. The plaque was shown to absorb the red color so that it becomes clearly visible on the tooth surface. Moreover, the red coloring could easily be rinsed off from the tooth surface. Accordingly, the presence of said natural dye made from sugar beets in a plaque-disclosing composition renders the plaque deposits on the teeth clearly and selectively visible to the user immediately upon contact therewith, and persists in the mouth to the degree desirable for plaque-disclosing purposes; but does not exhibit an excessively prolonged staining effect. The dye is easily removed from the teeth by simply rinsing, is pleasant tasting and non-toxic (approved by FDA), thereby providing an effective tool for diagnostic use and in self-help oral health programs.

The concentration of the sugar beet colorant in the plaque-disclosing vehicle is not critical and may vary from about 1% to 40% in liquid form, and from about 1 to 60% in powder form. The novel dye may be made available in a variety of compositions. For example, this novel dye can be formulated as a chewable tablet, wafer, powder, lozenges, aerosol, or liquid concentrate to be painted on full strength or diluted with water as a rinse.

The plaque disclosing vehicle preferably constitutes a major amount of a physiologically acceptable inert carrier or diluent for the dye which is preferably tasteless or pleasant tasting and odorless; or an aqueous solution thereof, depending on the final form of the disclosing composition. More specifically, the tablets or powder contain substantially no water, whereas the liquid concentrate or rinse comprises an aqueous solution thereof. The carrier functions to facilitate the solution of the dye in the oral cavity and to aid in the penetration of the dye into plaque deposits.

In addition to the active dye ingredient, tablets contain inert additives which help to impart satisfactory compression characteristics to the formulation including diluents, binders and lubricants. Any known carrier or diluent which is stable and compatible with the beet juice dye indicator and does not adversely affect the plaque disclosing properties thereof can be utilized, such as dicalcium phosphate, calcium sulfate, lactose, kaolin, sodium chloride, dry starch, powdered sugar, mannitol, sorbitol or the like, and mixtures thereof. However, sorbitol and/or mannitol are preferred diluents for chewable tablets because of their high water solubility and pleasant taste. The carrier or diluent constitutes the major ingredient of the tablet formulation and is present in amounts of about 40 to 95%, and preferably about 70 to 95% by weight.

In addition to the diluent, a tablet generally contains at least one binder or thickening agent to impart cohesive qualities to the powdered material. Materials commonly used as binders include starch; gelatin; sugars such as sucrose, glucose, dextrose, molasses and lactose; natural and synthetic gums such as gum acacia, sodium alginate, Irish moss, gum tragacanth, viscarin, hydroxyethylcellulose, carboxymethylcellulose, methylcellulose, polyvinylpyrrolidone, and the like or mixtures thereof. These thickening agents are generally present in an amount sufficient to impart cohesiveness to the formulation, more particularly in amounts of about 1 to 10% and preferably 2-5% by weight.

Another ingredient generally contained in a tablet is a lubricant which prevents adhesion of the tablet materials to the surface of the dies and punches, reduces interparticular friction during compression, and facilitates the ejection of the tablet from the die cavity. Again, compatibility with the active dye ingredient and stability are essential prerequisites. Suitable lubricants are well known and include magnesium stearate, calcium stearate, paraffin, stearic acid, cocoa butter, talc, boric acid, sodium chloride, and the like. The proportion of lubricant is generally in the range of about 0.1 to 5% by weight.

In the preparation of an aqueous disclosing composition, it is preferable to include about 30-40% by weight of glycerin or propylene glycol, which function as a suspending agent and thickener, and help in giving a sweeter taste to the formulation.

Normally the proportion of the vehicle is determined by the physical properties of the plaque-disclosing formulation. Usually, however, from about 40 to 95% of the vehicle will be employed, with about 40 to 95% being a typical range for the production of solid disclosing compositions such as tablets, wafers and powders, and about 60 to 95% being useful for the manufacture of liquid preparations such as concentrates or rinses.

Any suitable flavoring or sweetening sialagogues or mixture thereof may be employed in formulating a flavor for the compositions of the present invention. Examples of suitable flavoring constituents include the flavoring oils, e.g. oils of spearmint, peppermint, wintergreen, sassafras, clove, sage, eucalyptus, marjoram, cinnamon, lemon, lime, grapefruit and orange, as well as flavoring aldehydes, esters such as methyl salicylate, alcohols, and higher fatty compounds known in the art. Also useful are such chemicals as menthol, carvone and anethole. Of these, the most commonly employed are the oils of peppermint, spearmint, and eucalyptus and anethole, menthol and carvone. In some cases flavorful solvents, such as chloroform and mock chloroform, may be employed. Such flavorings may be used as liquids or may be solidified by being mixed with a particulate carrier material, such as starch, calcium carbonate, paraffin, vegetable wax, fat, higher fatty acid or other suitable carrier substances. In the cases of solid flavors, such as vanillin, sage, citric acid or licorice, the flavor may be converted to liquid form, if so desired, by dissolving it in the solvent or emulsifying it, usually with the help of a synthetic or natural emulsifying agent. The choice as to whether to utilize particulate solid or liquid flavors or to convert such flavors to a particulate solid or liquid form, respectively, will often depend on the properties desired in the flavor and its compatibility with the sweetener and any other material to be present with it. Suitable sweetening agents include sucrose, lactose, maltose, xylitol, sodium cyclamate, saccharin, the dipeptides of U.S. Pat. No. 3,939,261 and the oxathiazin salts of U.S. Pat. No. 3,932,606. Suitably, flavor and sweetening agent may together comprise from about 0.1 to 5% or more of the compositions of the instant invention.

Various other compatible and suitable materials may be incorporated in the plaque-disclosing compositions of this invention, in minor amounts of about 0.1 to 10% by weight. Examples thereof are preservatives such as sodium benzoate, methyl paraben, propyl paraben, potassium sorbate or mixtures thereof; thickeners and/or suspending (gelling) agents such as hydroxyethylcellulose 100,000 cps, carboxymethylcellulose, viscarin, sodium alginate and the like or mixtures thereof. These adjuvants are incorporated into the instant compositions in amounts which do not substantially adversely affect the properties and characteristics desired, and are selected and used in proper amounts depending upon the particular type of preparation involved.

The present plaque disclosing compositions may be prepared by suitably mixing the ingredients. For instance in making an aqueous solution thereof, the liquid beet juice colorant is simply dissolved in water, to which may optionally be added other water-soluble ingredients such as preservative, sweeteners, flavors, thickeners or suspending agents including glycerin or the like. A water-soluble liquid carrier such as glycerin is preferably admixed with the water prior to the addition of the beet juice colorant, and a suitable thickening agent mixed therewith until the mixture is homogeneous.

In the preparation of the composition in powdered form, it is usually sufficient to admix mechanically, the various solid ingredients, namely the inert carrier, the vegetable dye coloring, flavor, etc., in appropriate quantities and particle sizes.

In the preparation of chewable dental tablets or wafers, the solid ingredients are admixed mechanically as above, and included in said mixture is a tabletting aid to facilitate the formation of a tablet. A sufficient amount of liquid such as ethyl alcohol is added to moisten and form granules. The granules are dried and then compressed into tablets of the desired size and shape.

In the preparation of aerosol sprays, a suitable non-toxic propellant or mixture of propellants are added to the liquid composition, in amounts of 5 to 50% of the total composition. Suitable propellants are halogen-substituted hydrocarbon compounds available from E. I. DuPont de Nemours Company and known as Freons.

The following Examples are given to illustrate this invention further. In this application all proportions are by weight unless indicated otherwise.

EXAMPLE 1

| Plaque Disclosing Tablets | |
|---|---|
| Ingredient | Quantity/tablet (mg) |
| Mannitol U.S.P. | 110.00 |
| Sorbitol U.S.P. | 235.73 |
| Polyvinylpyrrolidone | 12.00 |
| Magnesium stearate | 4.50 |
| Red vegetable dye powder (Color-Treme R-333) | 7.40 |
| Strawberry Flavor | 0.37 |
| | 370.00 Total weight/tablet |

All the above listed ingredients are passed through a 60 mesh sieve, placed in a roller mixer and mixed for 30 minutes. Just enough ethyl alcohol is added to moisten and form granules. The mixture is dried overnight at 50° C. and subsequently compressed into tablets using a ⅜ inch die.

The resulting tablets which contain 2% of the Color-Treme dye are white with red specks, and have acceptable favor and odor.

The user chews the tablet until dissolved, mixed with the saliva and swished around in the mouth for about ½ minute and preferably expectorated. Upon examination of the teeth with a mirror, the plaque stains red. The red-stained plaque is brushed clean and the procedure repeated for several days until no red-stained plaque is visible on the teeth.

EXAMPLE 2

Example 1 is repeated except that 1.11 mg sodium saccharin is added, the Color-Treme content is reduced to 3.70 mg (1%) and the sorbitol is increased to 238.32 mg.

These tablets are also white with red specks and have acceptable sweetness, flavor and odor for consumer use.

EXAMPLE 3

Example 2 is repeated except that the Color-Treme content is increased to 37.0 mg (10%) and the sorbitol content is reduced accordingly.

The resultant tablets are similar in appearance and have the same acceptable physical characteristics of flavor, sweetness and odor as above.

EXAMPLE 4

Example 2 is repeated except that the Color-Treme content is increased to 74.0 mg (20%) and the sorbitol content is reduced accordingly.

These tablets are similar in appearance and in physical characteristics as in Example 3.

EXAMPLE 5

| Plaque Disclosing Solution | |
|---|---|
| Ingredient | Quantity |
| Sodium Benzoate | 83.0 mg |
| Sodium Saccharin | 100.0 mg |
| Color-Treme R-111 (beet juice Concentrate) | 11.0 ml |
| Glycerine (99.5%) | 35.39 gm |
| Strawberry Flavor | 125.0 mg |
| Hydroxyethylcellulose (100,000 cps) | 120.0 mg |
| Distilled water q.s. | 100.0 ml |

The sweetener sodium saccharin, is dissolved in 60 ml distilled water in a mixer. The sodium benzoate is dissolved in a small amount of water and added to the saccharin solution. The glycerin is added to the mixer, followed by the Color-Treme and the flavor. The hydroxyethylcellulose thickener and the rest of the water are added and the solution mixed until it is homogeneous.

The resultant solution has a pleasant taste, selectively stains plaque deposits, and is easy to rinse off.

A small amount (several drops) are placed under the tongue, mixed with the saliva and swished around between the teeth for ½ minute and swallowed or expectorated. Examination of the teeth with a mirror reveals the red-stained plaque which is brushed clean and the procedure repeated until no more red-stained plaque is visible on the teeth.

Other examples may be compounded in the form of a lozenge, gel, wafer, powder and aerosol by utilizing the appropriate additives such as a solid corn syrup or similar base for lozenges; a gelling agent such as the natural and synthetic gums and gum-like materials for a gel; and propellants for an aerosol. Suitable gelling agents include sodium carboxymethylcellulose, hydroxyethylcellulose, polyvinyl alcohol, Irish moss, Silica aerogel, and the like and mixtures thereof.

Still other examples may be compounded wherein the flavor or flavors are changed to peppermint, spearmint, eucalyptus, anethole, menthol, carvone, lemon, orange, etc., and the proportions varied over a 0.1 to 5% range and preferably 0.5 to 2% for best taste effects.

Similarly, preservatives other than sodium benzoate may be used, as well as other tabletting lubricants such as calcium stearate and the like.

It is understood that the foregoing detailed description is given merely by way of illustration and that variations may be made therein without departing from the spirit of the invention. The "Abstract" given above is merely for the convenience of technical searchers and is not to be given any weight with respect to the scope of the invention.

I claim:

1. A method of identifying and locating plaque deposits in the oral cavity which comprises selectively staining said plaque formation on tooth surfaces without staining the adjacent oral tissues by means of applying to said oral cavity a plaque disclosing composition containing an effective staining amount of the red vegetable dye obtained from sugar beets consisting essentially of the red betamine color component and the yellow vulgaxanthin color component in the ratio of 1.9 to 1 whereby the plaque deposits absorb said red dye to identify the areas of plaque formation which is clearly visible to the naked eye as red-stained plaque, immediately upon contact and easily removable therefrom by rinsing.

2. A method in accordance with claim 1, wherein said disclosing composition is an aqueous solution comprising about 30–40% by weight of glycerin or propylene glycol.

3. A method in accordance with claim 1, wherein said disclosing composition is a substantially water-free, water-soluble, physiologically acceptable inert solid comprising about 40–95% by weight of a stable carrier for said sugar beet dye which is compatible with said dye and does not adversely affect the plaque disclosing properties of said dye.

4. A method in accordance with claim 3, wherein said solid is in the form of a chewable tablet and the carrier is selected from the group consisting of sorbitol and mannitol and mixtures thereof.

5. A method in accordance with claim 1, wherein said disclosing composition is in the form of an aerosol spray comprising about 5–50% non-toxic propellants.

* * * * *